United States Patent
Fan et al.

(10) Patent No.: US 9,020,609 B2
(45) Date of Patent: *Apr. 28, 2015

(54) ELECTRODE LEAD OF PACEMAKER AND PACEMAKER USING THE SAME

(75) Inventors: Li Fan, Beijing (CN); Chen Feng, Beijing (CN); Wen-Mei Zhao, Beijing (CN); Liang Liu, Beijing (CN); Yu-Quan Wang, Beijing (CN); Li Qian, Beijing (CN)

(73) Assignees: Tsinghua University, Beijing (CN); Hon Hai Precision Industry Co., Ltd., New Taipei (TW)

( * ) Notice: Subject to any disclaimer, the term of this patent is extended or adjusted under 35 U.S.C. 154(b) by 202 days.

This patent is subject to a terminal disclaimer.

(21) Appl. No.: 13/527,808

(22) Filed: Jun. 20, 2012

(65) Prior Publication Data

US 2013/0110214 A1 May 2, 2013

(30) Foreign Application Priority Data

Oct. 28, 2011 (CN) .......................... 2011 1 0333569

(51) Int. Cl.
  *A61N 1/00* (2006.01)
  *A61N 1/05* (2006.01)
(52) U.S. Cl.
  CPC ............... *A61N 1/056* (2013.01); *A61N 1/0565* (2013.01); *A61N 1/057* (2013.01)
(58) Field of Classification Search
  USPC ....................................... 607/5, 119; 600/373
  See application file for complete search history.

(56) References Cited

U.S. PATENT DOCUMENTS

| | | | |
|---|---|---|---|
| 3,893,461 A * | 7/1975 | Preston | 607/17 |
| 5,713,945 A | 2/1998 | Fischer et al. | |
| 7,493,160 B2 * | 2/2009 | Weber et al. | 607/3 |
| 7,596,415 B2 | 9/2009 | Brabec et al. | |
| 8,825,178 B2 * | 9/2014 | Feng et al. | 607/119 |
| 2004/0051432 A1 | 3/2004 | Jiang et al. | |
| 2006/0272701 A1 * | 12/2006 | Ajayan et al. | 136/263 |
| 2009/0062895 A1 | 3/2009 | Stahmann et al. | |
| 2009/0187236 A1 * | 7/2009 | Marshall et al. | 607/126 |
| 2009/0194313 A1 | 8/2009 | Jiang et al. | |
| 2009/0255706 A1 | 10/2009 | Jiang et al. | |
| 2009/0312825 A1 * | 12/2009 | Keitel et al. | 607/127 |
| 2010/0147829 A1 * | 6/2010 | Liu et al. | 219/546 |
| 2011/0140309 A1 * | 6/2011 | Liu et al. | 264/400 |
| 2011/0301657 A1 * | 12/2011 | Walsh et al. | 607/5 |
| 2012/0271394 A1 | 10/2012 | Foster et al. | |

FOREIGN PATENT DOCUMENTS

| | | |
|---|---|---|
| CN | 1484275 | 3/2004 |
| CN | 1943805 | 4/2007 |
| CN | 101499331 | 8/2009 |
| CN | 101757723 | 6/2010 |

(Continued)

*Primary Examiner* — Niketa Patel
*Assistant Examiner* — William Levicky
(74) *Attorney, Agent, or Firm* — Novak Druce Connolly Bove + Quigg LLP (57) ABSTRACT

An electrode lead of a pacemaker includes at least one lead wire including at least one composite conductive core. The at least one composite conductive core includes at least one conductive core and at least one carbon nanotube yarn spirally wound on an outer surface of the at least one conductive core. The at least one carbon nanotube yarn includes a number of carbon nanotubes joined end to end by van der Waals attractive forces. The pacemaker includes a pulse generator and the electrode lead electrically connected to the pulse generator.

17 Claims, 11 Drawing Sheets

(56) References Cited

FOREIGN PATENT DOCUMENTS

| | | |
|---|---|---|
| CN | 101925379 | 12/2010 |
| TW | 200945372 | 11/2009 |
| TW | 201039670 | 11/2010 |
| TW | I345792 | 7/2011 |

* cited by examiner

ELECTRODE LEAD OF PACEMAKER AND PACEMAKER USING THE SAME

This application claims all benefits accruing under 35 U.S.C. §119 from China Patent Application No. 201110333485.2, filed on Oct. 28, 2011, in the China Intellectual Property Office, the contents of which are hereby incorporated by reference. This application is related to common-assigned applications entitled, "METHOD FOR MAKING PACEMAKER ELECTRODE LEAD," filed on Jun. 20, 2012, and application Ser. No. 13/527,780; "ELECTRODE LEAD OF PACEMAKER AND PACEMAKER USING THE SAME,"on Jun. 20, 2012, and application Ser. No. 13/527,782; "ELECTRODE LEAD OF PACEMAKER AND PACEMAKER USING THE SAME"on Jun. 20, 2012, 2011, and application Ser. No. 13/527,784; "PACEMAKERS AND PACEMAKER LEADS" filed on Jun. 20, 2012, and application Ser. No. 13/527,792; "PACEMAKERS AND PACEMAKER LEADS" filed on Jun. 20, 2012, and application Ser. No. 13/527,801; "ELECTRODE LEAD OF PACEMAKER AND PACEMAKER USING THE SAME" filed on Jun. 20, 2012, and application Ser. No. 13/527,820; "PACEMAKER ELECTRODE LEAD AND PACEMAKER USING THE SAME" filed on Jun. 20, 2012, and application Ser. No. 13/527,836; "PACEMAKER ELECTRODE LEAD AND PACEMAKER USING THE SAME" filed on Jun. 20, 2012, and application Ser. No. 13/527,849.

BACKGROUND

1. Technical Field

The present disclosure relates to an electrode lead of a pacemaker and a pacemaker using the same.

2. Description of Related Art

A pacemaker is an electronic therapeutic device that can be implanted in living beings such as humans. The pacemaker includes a battery, a pulse generator, and an electrode lead. The pulse generator is used to emit a pulsing current, via the electrode lead, to stimulate a diseased organ such as a human heart, to work normally.

The electrode lead usually includes a lead wire made from metal or alloy. However, a mechanical strength and toughness of the lead wire decreases as the diameter decreases. The violence of a fierce seizure suffered by a patient or even the energetic long-term normal activities of the patient may cause damage to the implanted electrode lead, or the electrode lead may even be broken. Therefore, a working life of the electrode lead and of the pacemaker will be decreased, and safety of the patient may be threatened.

What is needed, therefore, is to provide an electrode lead of a pacemaker which has good mechanical strength, toughness, and small physical size, to improve the working life of the electrode lead and the pacemaker using thereof.

BRIEF DESCRIPTION OF THE DRAWING

Many aspects of the present disclosure can be better understood with reference to the following drawings. The components in the drawings are not necessarily to scale, the emphasis instead being placed upon clearly illustrating the principles of the present embodiments.

DETAILED DESCRIPTION

The disclosure is illustrated by way of example and not by way of limitation in the figures of the accompanying drawings in which like references indicate similar elements. It should be noted that references to "another," "an," or "one" embodiment in this disclosure are not necessarily to the same embodiment, and such references mean at least one.

Figure 1:
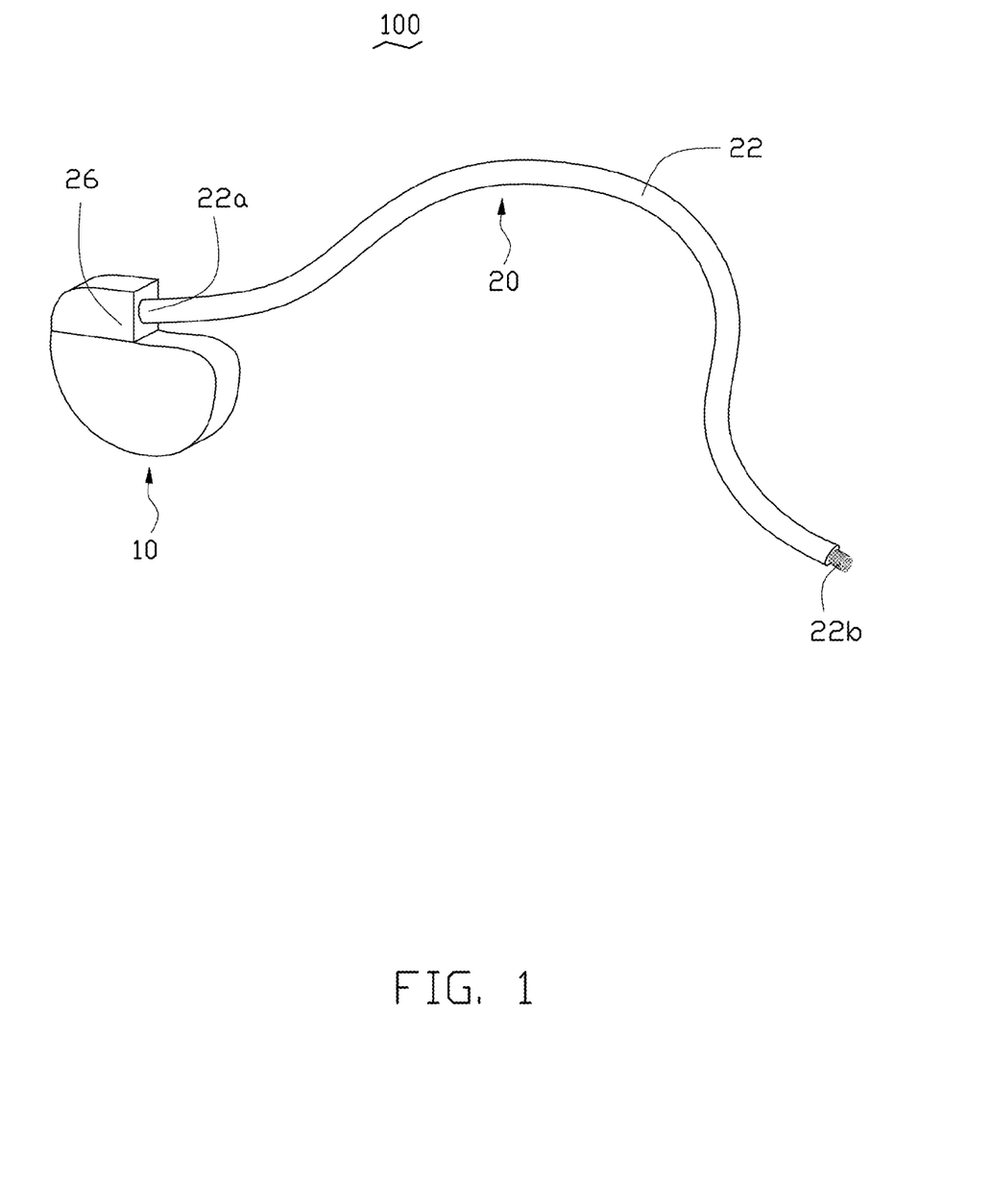
FIG. 1 is a view of one embodiment of a pacemaker.

Referring to FIG. 1, one embodiment of a pacemaker 100 includes a pulse generator 10 and an electrode lead 20 electrically connected with the pulse generator 10. The pulse generator 10 can be used to generate pulse signals to stimulate organs of living beings via the electrode lead 20.

The pulse generator 10 can include a shell (not labeled), a power source (not shown) and a control circuit (not shown). The power source and the control circuit are packaged in the shell. The power source can provide power for the control circuit. Batteries can be used as the power source, such as lithium ion batteries, fuel cells, and physical power batteries. In one embodiment, a lithium-iodine battery is the power source. The control circuit can include an output circuit and a sensing circuit. The output circuit can be used to generate the pulse signals. The sensing circuit can be used to receive electrical signals generated by the stimulated organs and feed these electrical signals back to the output circuit. The output circuit can adaptively adjust to output proper pulse signals according to the feedback of the sensing circuit. The organs can be a heart, brain, or stomach of living beings. In one embodiment, the organ is the heart of a human being. The pulse signals can be a square wave pulsing current. A pulse width of the pulse signals can be in a range from about 0.5 milliseconds to about 0.6 milliseconds. The pulse current can be generated by a charging-discharging process of a capacitor in the control circuit. The shell used for packaging can prevent an interaction between the power source, the control circuit and the living being in which the pacemaker is implanted. A material of the shell can be a metal or alloy having inertness in the sense of biological compatibility, corrosion resistance, and toughness or rigidity of structure. In one embodiment, the material of the shell is titanium.

Figure 2:
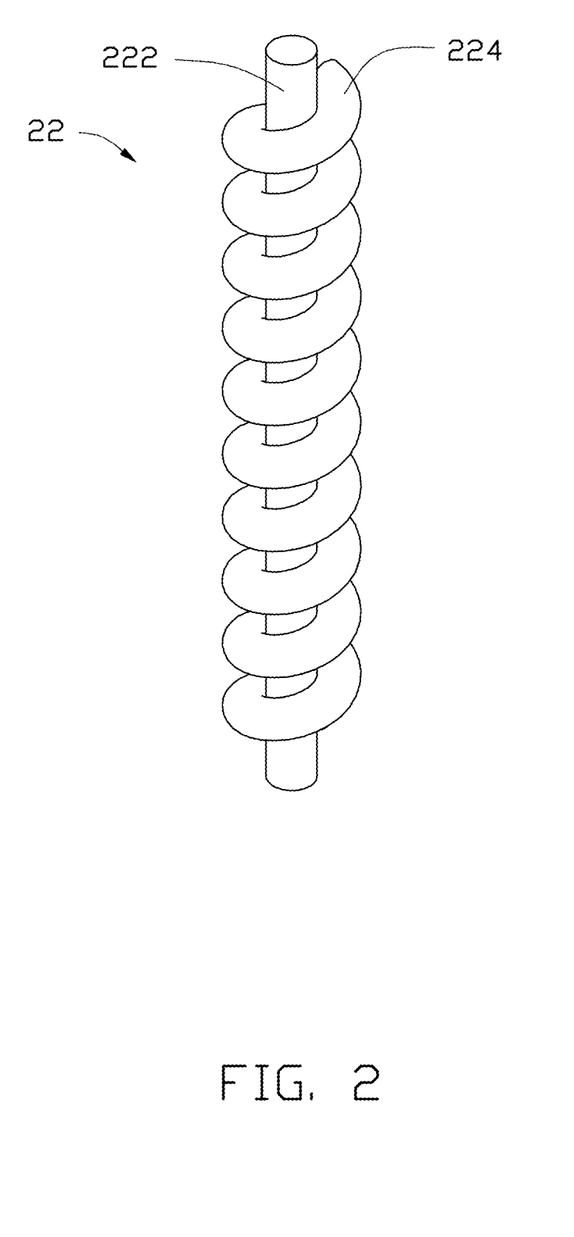
FIG. 2 is a view of an embodiment of a lead wire of the pacemaker.

Referring FIG. 1 and FIG. 2, the electrode lead 20 can include at least one lead wire 22. The lead wire 22 has two ends opposite to each other along the extending direction of the lead wire 22. One end of the lead wire 22 is defined as a proximal end 22a, and the other end of the lead wire 22 is defined as a distal end 22b. The proximal end 22a is near and electrically connected with the pulse generator 10. The distal end 22b directly contacts the diseased organs needing stimulation.

The lead wire 22 can include at least one linear conductive core 222 and at least one carbon nanotube yarn 224 spirally wound on an outer surface of the conductive core 222.

The conductive core 222 supports the carbon nanotube yarn 224. The conductive core 222 can be hollow or a cylindrical structure of solid material. A material of the conductive core 222 can be a metal or a composite formed of metal and other conductive materials. The metal can be MP35N, 35NLT, stainless steel, carbon fiber, tantalum, titanium, zirconium, niobium, titanium alloy, copper, silver, platinum, platinum-yttrium alloy, or platinum-palladium alloy. MP35N is an alloy including 35Co-35Ni-20Cr-10Mo, and titanium is about 1% by weight in the alloy. 35NLT is also an alloy including 35Co-35Ni-20Cr-10Mo, and the percentage of titanium is about 0.01% by weight in the alloy. The composite can be a composite of metal and carbon fiber. In one embodiment, the material of the conductive core 222 is platinum.

The at least one carbon nanotube yarn 224 can be a non-twisted carbon nanotube yarn, a twisted carbon nanotube yarn, or any combination thereof.

Figure 3:
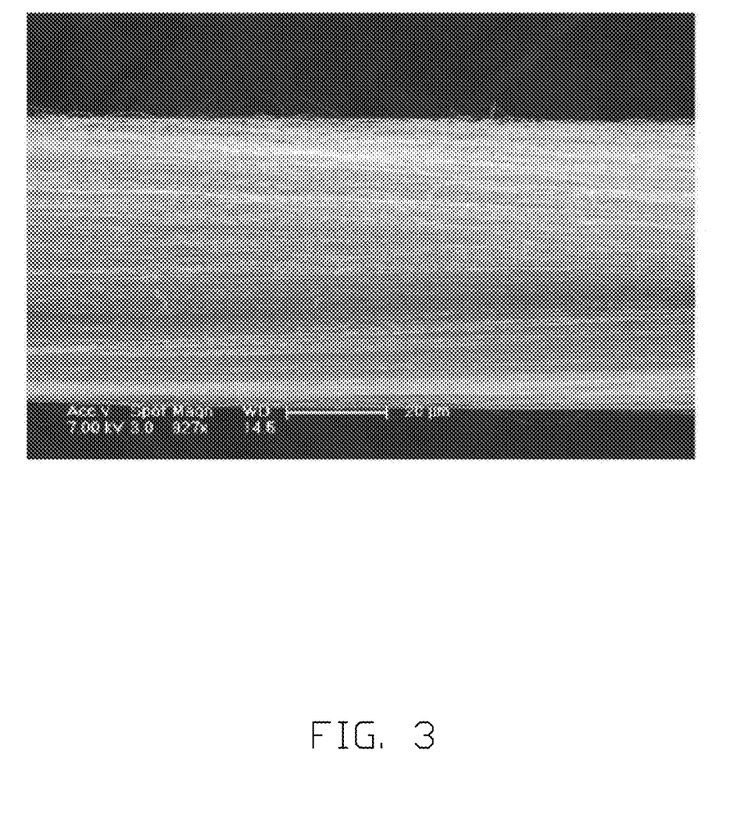
FIG. 3 shows a Scanning Electron Microscope (SEM) image of a non-twisted carbon nanotube yarn.

Referring to FIG. 3, the non-twisted carbon nanotube yarn is a free-standing or stiff structure consisting of a plurality of carbon nanotubes. A majority of the plurality of carbon nanotubes extend in substantially the same direction and parallel to each other. In addition, the majority of the carbon nanotubes are joined end to end by van der Waals attractive forces. Each carbon nanotube in the majority of the carbon nanotubes is joined with the adjacent carbon nanotube lengthwise by van der Waals attractive forces. A minority of the plurality of carbon nanotubes has a random orientation in the non-twisted carbon nanotube yarn, and has a very small or negligible effect on the majority of the carbon nanotubes. The non-twisted carbon nanotube yarn includes a plurality of successive and preferred-orientation carbon nanotube segments. The plurality of carbon nanotube segments are joined end to end by van der Waals attractive forces. Each of the carbon nanotube segments includes a plurality of carbon nanotubes substantially parallel with each other. The carbon nanotubes in parallel are joined side by side by van der Waals attractive forces. The free-standing or stiff structure of the non-twisted carbon nanotube yarn is a result of van der Waals attractive forces acting on the carbon nanotubes joined end to end and side by side. A diameter of the non-twisted carbon nanotube yarn can be in a range from about 0.5 nanometers to about 100 microns.

The non-twisted carbon nanotube yarn can be formed by the steps of: S(a), choosing a carbon nanotube segment having a predetermined width from a carbon nanotube array by a drawing tool; and S(b), moving the drawing tool to pull the chosen carbon nanotube segment at a predetermined speed, thereby pulling out a continuous carbon nanotube yarn including the plurality of carbon nanotube segments joined end-to-end by van der Waals attractive forces therebetween. Examples of the non-twisted carbon nanotube wire are taught by US Patent Application Publication US 2007/0166223 to Jiang et al.

Figure 4:
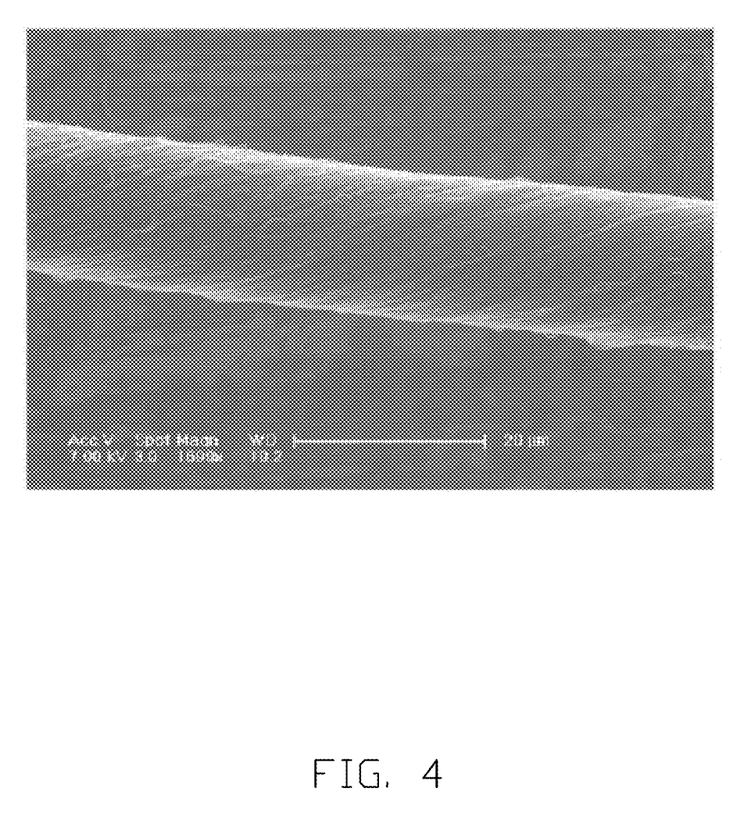
FIG. 4 shows a SEM image of a twisted carbon nanotube yarn.

Referring to FIG. 4, the twisted carbon nanotube yarn can be formed by twisting the non-twisted carbon nanotube yarn by using a mechanical force to turn the two ends of the non-twisted carbon nanotube yarn in opposite directions. The twisted carbon nanotube yarn includes a plurality of carbon nanotubes oriented around the central axis of the twisted carbon nanotube yarn. The carbon nanotubes are aligned helically around the central axis of the twisted carbon nanotube yarn.

The non-twisted carbon nanotube yarn and the twisted carbon nanotube yarn can be treated with a volatile organic solvent. After being soaked by the organic solvent, the carbon nanotubes which are adjacent and substantially parallel to each other in the non-twisted or twisted carbon nanotube yarn will bundle together, due to the surface tension of the organic solvent when the organic solvent volatilizes. A specific surface area and a viscosity of the carbon nanotube yarn will decrease, and a density and strength of the carbon nanotube yarn will increase. A tensile strength of the twisted carbon nanotube yarn can be greater than 1200 Mega Pascals (MPa). The tensile strength can reach 1.5 Giga Pascals (GPa), if the diameter of the twisted carbon nanotube yarn decreases to 10 microns. The volatile organic solvent can be ethanol, methanol, acetone, dichloroethane, chloroform, or any combination thereof. In one embodiment, the volatile organic solvent is ethanol. The carbon nanotube yarn 224 can be a pure carbon nanotube structure. The pure carbon nanotube structure consists of pristine carbon nanotubes. The characterization "pristine" signifies that the carbon nanotubes are unfunctionalized or not chemically modified.

The at least one carbon nanotube yarn 224 can include a plurality of yarns 224 to increase the strength. The plurality of carbon nanotube yarns 224 can be attached together, relatively straight, and substantially parallel to each other. A twisted cable can be formed by twisting the plurality of carbon nanotube yarns 224 together.

The at least one carbon nanotube yarn 224 is spirally wound on the outer surface of the conductive core 222 to form a composite conductive core. The at least one carbon nanotube yarn 224 can be spirally wound on the outer surface of the conductive core 222 so as to completely cover the outer surface of the conductive core 222. More specifically, a length of the spirally wound carbon nanotube yarn 224, along the extending direction of the conductive core 222, can be substantially equal to the length of the conductive core 222. In addition, the spirally wound carbon nanotube yarn 224 can be longer than the conductive core 222 along the extending direction of the conductive core 222. The spirally wound carbon nanotube yarn 224 can extend beyond the distal end 22b of the lead wire 22 with respect to the conductive core 222, such that the carbon nanotube yarn 224 can directly contact the living organ at the distal end 22b. A sensing area of the electrode lead 20 will increase due to a large surface area of the carbon nanotube yarn 224 at or beyond the distal end 22b. Therefore, a sensitivity of the pacemaker 100 can be increased and thus improved correspondingly.

As the carbon nanotube yarn 224 is sticky, the carbon nanotube yarn 224 can directly adhere on the outer surface of the line-shaped conductive core 222 without a binder after the spiral winding. A screw pitch of the spirally wound carbon nanotube yarn 224 can be in a range from about 0 microns to about 5 microns. The pitch can be increased gradually from the proximal end 22a to the distal end 22b. If a patient, with the pacemaker 100 implanted therein, suffers a physical abnormal pain such as a fierce seizure, a typical conductive core 222 is fragile and can easily damage. However, the carbon nanotube yarn 224 is harder to break due to a good flexibility. In addition, a gradually increasing screw pitch of the carbon nanotube yarn 224 can provide a varied elasticity and thus greater deformability of the lead wire 22 when stretched or bent. Therefore, the chance of injury to the organs of the patient due to an excessively brittle lead wire 22 can be decreased.

Figure 5:
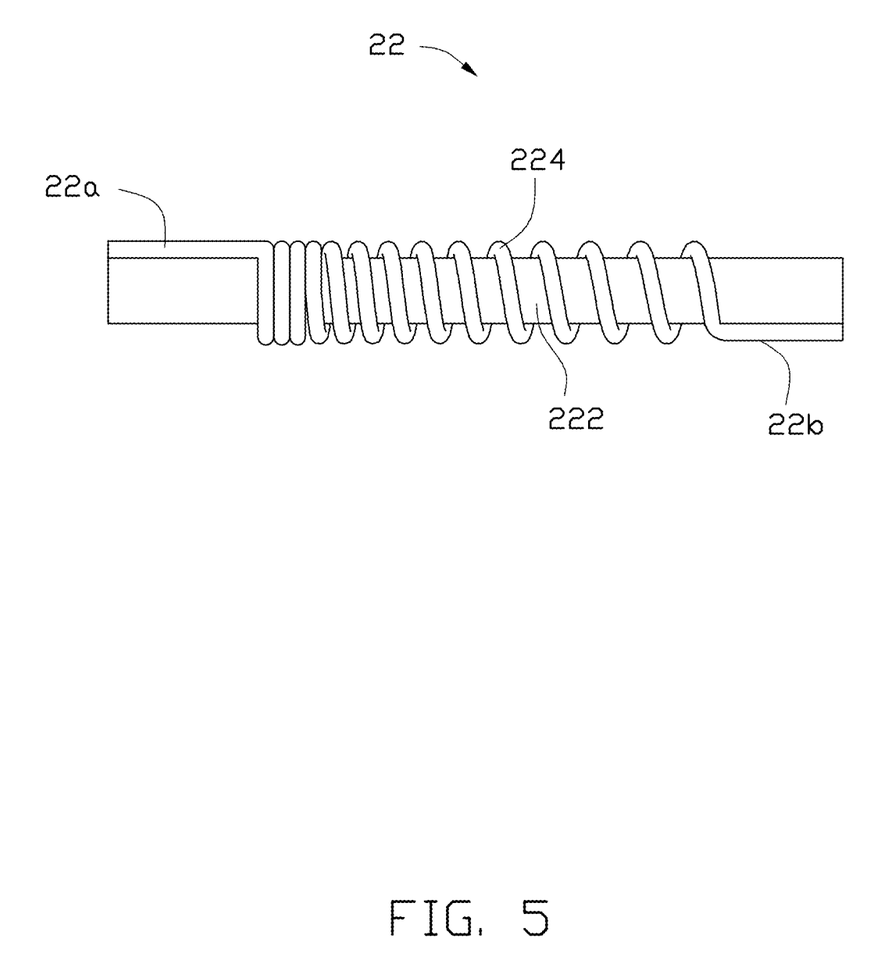
FIG. 5 is a view of an embodiment of the lead wire with the carbon nanotube yarn partly spirally wound thereon.

Referring to FIG. 5, some carbon nanotube yarns 224 or some portions of the carbon nanotube yarn 224 can be spirally wound on the outer surface of the conductive core 222. For example, a middle portion of the carbon nanotube yarn 224 along the extending direction can be spirally wound on the outer surface of the conductive core 222. In this structure, a portion of the carbon nanotube yarn 224 at the proximal end 22a, the distal end 22b, or both, can directly adhere on the outer surface of the conductive core 222 along the extending direction. In other words, the portion of the carbon nanotube yarn 224 at the proximal end 22a, the distal end 22b, or both is substantially parallel with the extending direction of the conductive core 222. In one embodiment, the carbon nanotube yarn 224 at both the proximal end 22a and the distal end 22b is substantially parallel with the extending direction of the conductive core 222. The carbon nanotube yarn 224 can protrude at the distal end 22b with respect to the conductive core 222 such that the carbon nanotube yarn 224 directly contacts the organ. The plurality of carbon nanotubes in the distal end 22b has a large specific surface area. Therefore, the lead wire 22 can have a large sensing area in the distal end 22b which can increase the sensitivity of the pacemaker 100. In addition, the carbon nanotubes at the proximal end 22a can be directly connected with the pulse generator 10 along the central axis thereof. Therefore, a signal transmitting efficiency can be improved by a good conductivity of the carbon nanotubes along the central axis.

The mechanical strength and the toughness of the lead wire 22 can be increased by the spirally wound carbon nanotube yarn 224 on the outer surface of the conductive core 222. More specifically, if the lead wire 22 is stretched by a drawing force, the conductive core 222 will be elongated along the stretching direction. The carbon nanotube yarn 224 being spirally wound can prevent the conductive core 222 from being broken due to a friction force between the carbon nanotube yarn 224 and the conductive core 222. Even if the conductive core 222 is fractured, the carbon nanotube yarn 224 will not be broken because of its good mechanical strength, and the pulse signals can still be transmitted through the carbon nanotube yarn 224 to the organ. The stimulating and sensing process can also be accomplished by the carbon nanotube yarn 224. Therefore, the pacemaker 100 still can work, and a working life of the pacemaker 100 can be prolonged.

Figure 6:
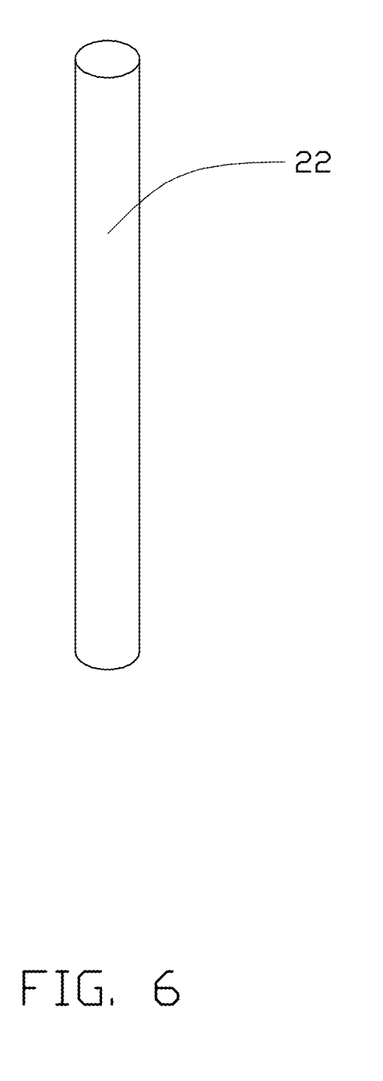
FIG. 6 is a view of an embodiment of the lead wire pulled straight.
Figure 7:
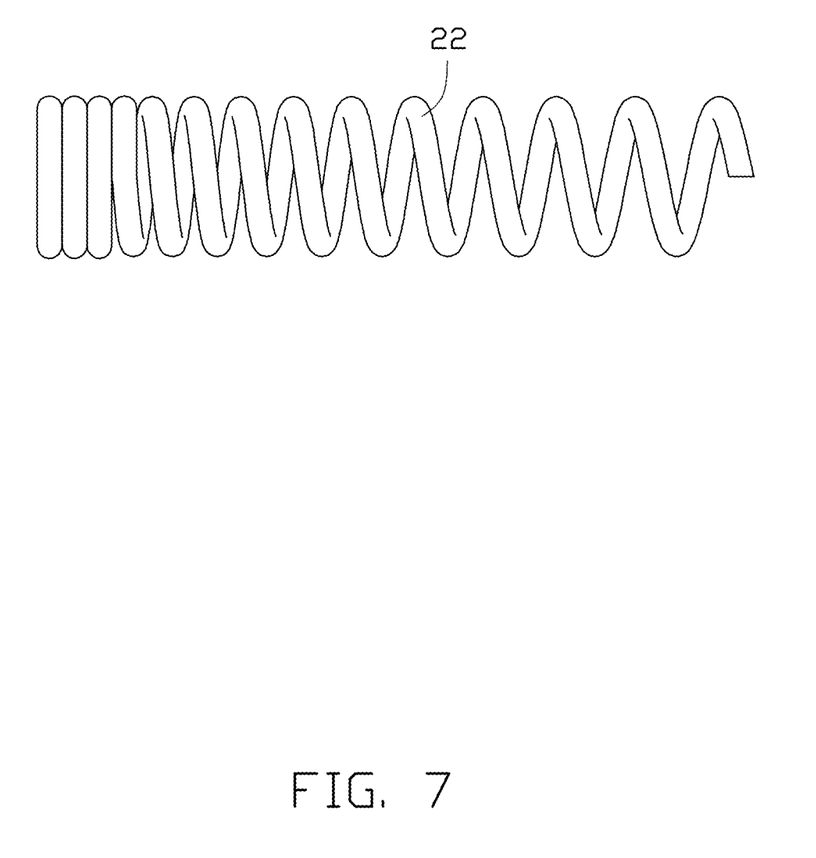
FIG. 7 is a view of an embodiment of the lead wire with a helical structure.

Referring to FIG. 6, the lead wire 22 can be a hollow structure or can be solid. Referring to FIG. 7, the lead wire 22 can also have a helical structure like a coil spring. The helical lead wire 22 possesses good elasticity. Therefore, the working life of the electrode lead 20 can be increased. The helical lead wire 22 can be formed by spirally winding a straight lead wire 22. More specifically, the helical lead wire 22 can be made by spirally winding a straight lead wire 22 on a rod-like support and removing the rod-like support to obtain the helical lead wire 22. The helical lead wire 22 forms a plurality of coils. A diameter across the coiling can be in a range from about 2 microns to about 6 microns. In one embodiment, the diameter across the coiling is about 5 microns. A screw pitch of the lead wire 22 can be in a range from about 0 microns to about 10 microns. Different screw pitches of the helical lead wire 22 can be formed along the extending direction from the proximal end 22a to the distal end 22b. In one embodiment, the screw pitch is gradually increased from the proximal end 22a to the distal end 22b. The gradually increasing screw pitch can accommodate stretching and shrinking of the lead wire 22, and thus can prevent a damage to an organ undergoing spasms. The screw pitch of the lead wire 22 in the proximal end 22a can be in a range from about 0 microns to about 3 microns. The screw pitch in the distal end 22b can be in a range from about 5 microns to about 8 microns.

Figure 8:
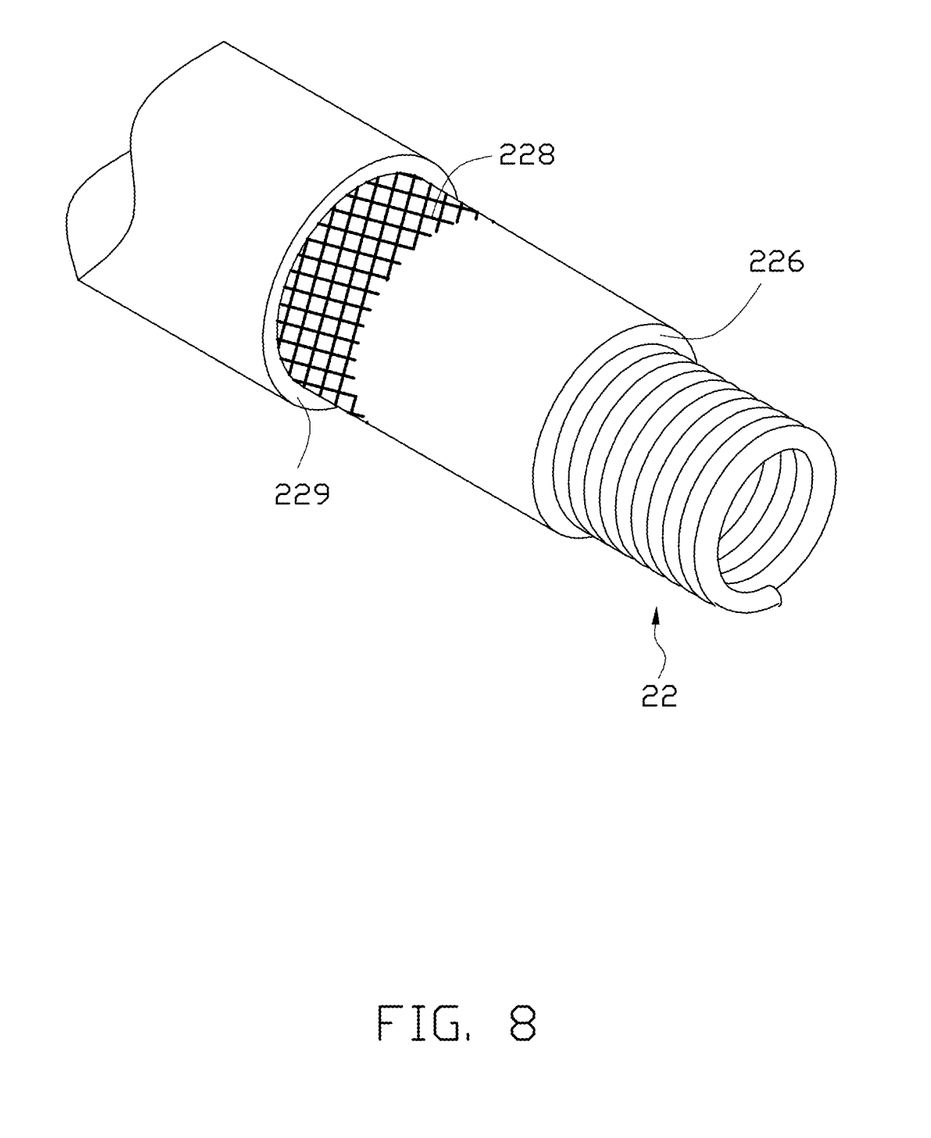
FIG. 8 is a sectional view of an embodiment of the lead wire with some layers peeled away.

Referring to FIG. 8, the lead wire 22 can further include an insulating layer 226 coated on a surface of the composite conductive core, the lead wire 22 being left naked in the distal end 22b. The insulating layer 226 can be fabricated by a flexible biocompatible material, such as silicon, polyurethane, polytetrafluoroethylene, or a copolymer of the silicon and polyurethane. In one embodiment, the material of the insulating layer 226 is silicon. A thickness of the insulating layer 226 can be in a range from about 1 micron to about 50 microns. The naked distal end 22b, as the contact end which stimulates, directly contacts the heart to transmit the pulse signals to the heart. The carbon nanotube yarn 224 has a large surface area. Therefore, the stimulating contact end can have a large sensing area to increase the sensitivity and sensing efficiency of the pacemaker 100.

The lead wire 22 can include a shielding layer 228 coated on an outer surface of the insulating layer 226. The shielding layer 228 can be a succession of films or a network structure. A material of the shielding layer 228 can be selected from the group consisting of metal, a carbon containing material, and combinations thereof. The carbon containing material can be a carbon fiber, graphene, carbon nanotubes, or combinations thereof.

The lead wire 22 can further include a coating layer 229 coated on an outer surface of the shielding layer 228 to protect the electrode lead 20. A material of the coating layer 229 can be the same as the material of the insulating layer 226. In one embodiment, the material of the coating layer 229 is silicon. A biologically-inert coating can be coated on an outer surface of the coating layer 229. The biologically-inert coating can increase the biological compatibility of the electrode lead 20 and can further be used as a bactericide or disinfectant. A material of the biologically-inert coating can be zirconia or zirconium nitride.

Figure 9:
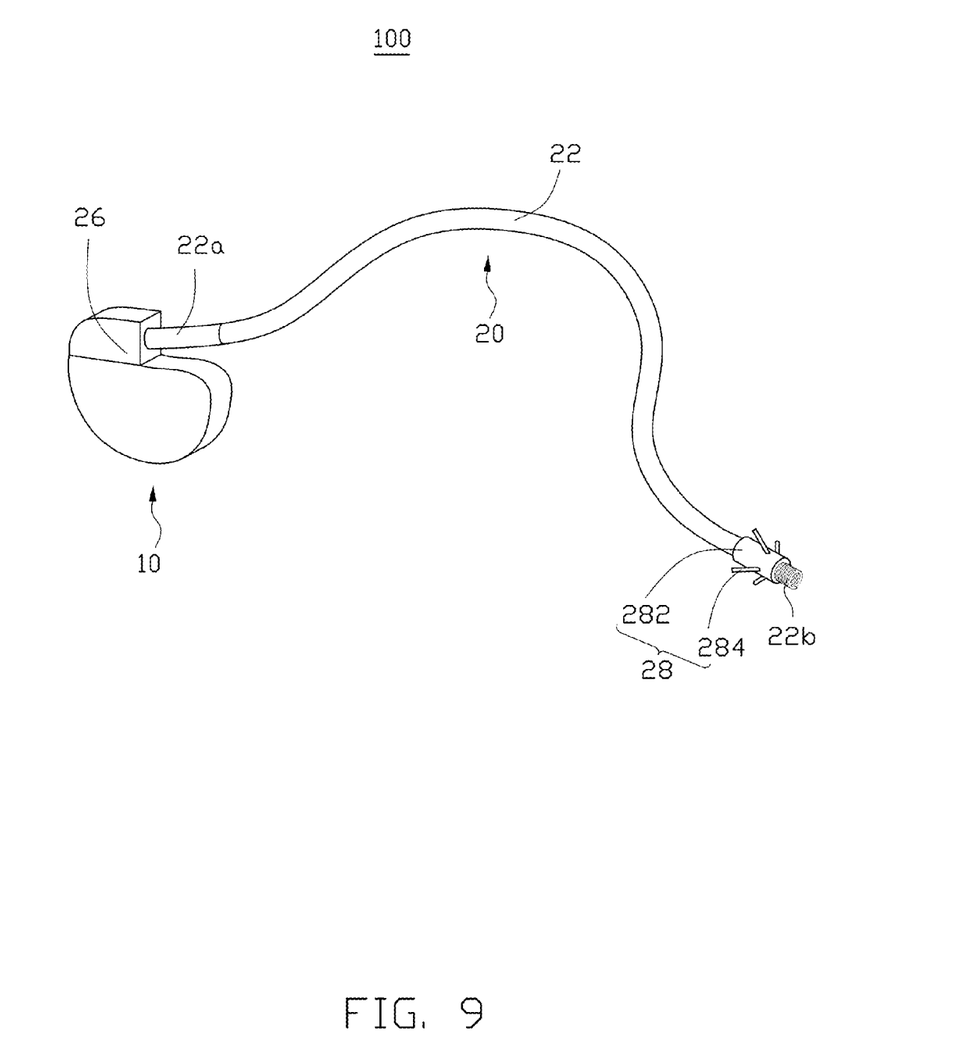
FIG. 9 is a view of an embodiment of the pacemaker with a connector and a fixture.

Referring to FIG. 9, the pacemaker 100 can further include a connector 26 and a fixture 28. The proximal end 22a of the lead wire 22 can be electrically connected with and affixed to the pulse generator 10 via the connector 26. The connector 26 can include a conductive contact member (not shown). The conductive contact member includes two opposite ends. One end of the conductive contact member is electrically connected and in contact with the control circuit in the pulse generator 10. The other end is electrically connected and in contact with the proximal end 22a of the lead wire 22. Thereby the lead wire 22 can be electrically connected with the control circuit in the pulse generator 10 to transmit the pulse signals. A material of the connector 26 can be the same as the material of the shell. In one embodiment, the material of the connector 26 is titanium. A material of the fixture 28 can be a polymer such as polyurethane or silicon rubber. The fixture 28 can include a fixing ring 282 and a plurality of fixing wings 284. The fixing ring 282 can be a cylindrical structure. The plurality of fixing wings 284 can be rod-shaped. The plurality of fixing wings 284 forms a branch axis diverging from a center line or axis of the fixing ring 282, to form a barb structure. A diverging direction deviates from the extending direction of the distal end 22b. An angle between the extending direction of each fixing wing 284 and the center line of the fixing ring 282 can be in a range from about 30 degrees to about 60 degrees. The distal end 22b is fixed to the organ by the fixing ring 282 to prevent the electrode lead 20 from moving or falling off the organ. The fixture 28 can also be a protrusion or helical structure as long as the electrode lead 20 can be tightly fixed in the diseased organ by fibrous tissues of the organ of living beings wrapping the fixture 28.

The connector 26 and the fixture 28 are not fundamental elements in the pacemaker 100. The proximal end 22a of the lead wire 22 can be directly connected with the control circuit. In addition, the distal end 22b of the lead wire 22 can be wrapped by the fibrous tissues of the organ of living beings to fix the electrode lead 20 in the target organ after a period of time after the electrode lead 20 has been implanted.

A working process of the pacemaker 100 acting on the heart of a human being is described below. A positive electrode of the power source is electrically connected with the shell, and a negative electrode of the power source is electrically connected with the control circuit. The pulse signals are generated by the pulse generator 10 and transmitted to the distal end 22b to stimulate the heart. A heartbeat frequency or a series of heartbeat frequencies can be sensed by detecting potential differences between the distal end 22b of the lead wire 22 and the shell. The potential differences are fed back to the control circuit to adjust the pulse signals to make the heart beat normally. In addition, a plurality of electrode leads 20 can be used to stimulate different organs in one human being.

Figure 10:
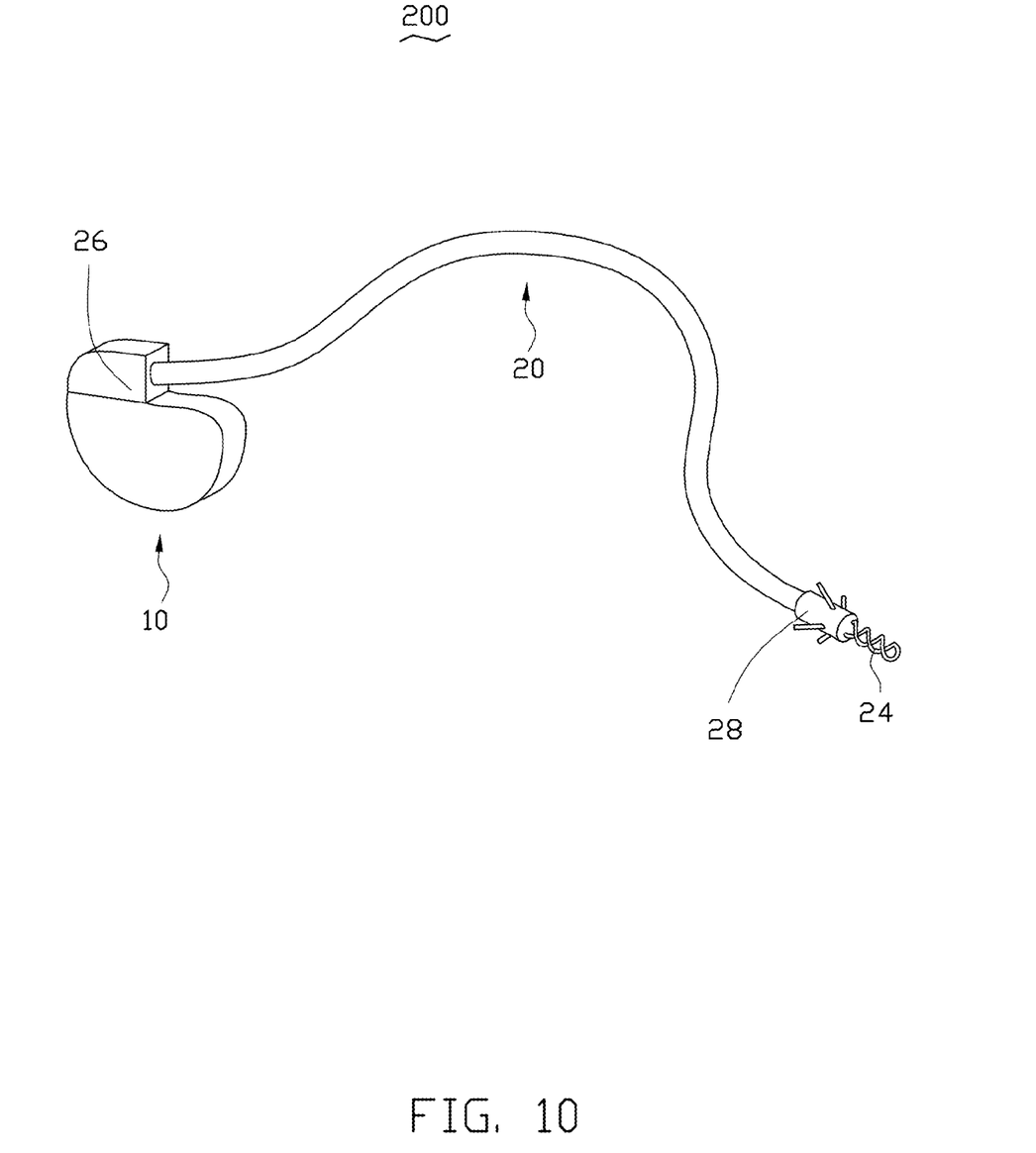
FIG. 10 is a view of another embodiment of a pacemaker.
Figure 11:
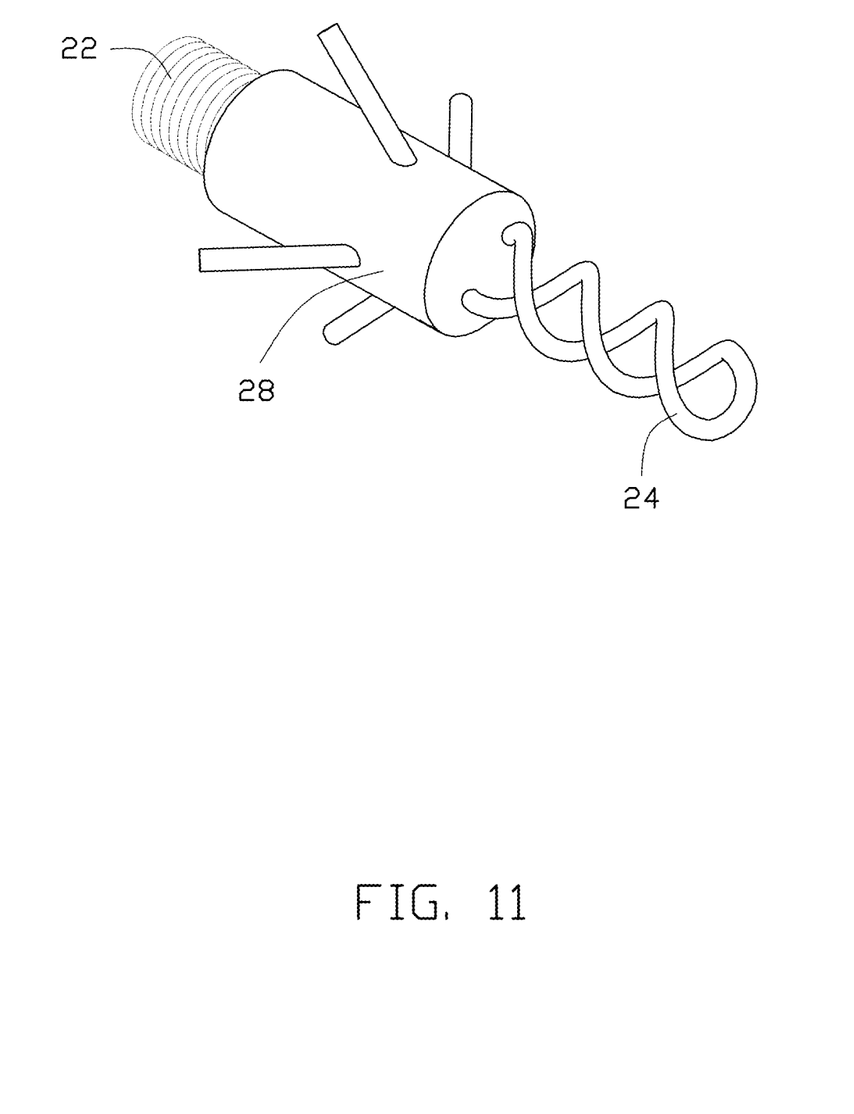
FIG. 11 is a view of an embodiment of an electrode tip of the pacemaker.

Referring to FIG. 10 and FIG. 11, another embodiment of a pacemaker 200 is provided. The structure of the pacemaker 200 is similar to the structure of the pacemaker 100. The difference between the two pacemakers is that the electrode lead 20 further includes an electrode tip 24 with two opposite ends. One end of the electrode tip 20 is electrically connected with the distal end 22b of the lead wire 22. The other end acts as a contact end to directly contact and stimulate the heart. The fixture 28 can protect and maintain the integrity of a joint between the electrode tip 24 and the distal end 22b of the lead wire 22. The lead wire 22 will function only as a pulse signal transmitter if the electrode tip 24 is used in the pacemaker. Under this situation, there will be no need for a naked distal end 22b of the lead wire 22. The electrode tip 24 can be an integrated structure. The electrode tip 24 can be cylindrical, helical, or ring-shaped. In one embodiment, the electrode tip 24 is helical. A length of the electrode tip 24 can be in a range from about 0.5 microns to about 2 microns. A material of the electrode tip 24 can be the same as the material of the composite conductive core or the conductive core 222. A porous material to ensure biocompatibility can be coated on an outer surface of the electrode tip 24. The porous material can increase the sensing area of the electrode tip 24, thereby increasing the sensitivity and sensing efficiency of the pacemaker 200.

Finally, it is to be understood that the above-described embodiments are intended to illustrate rather than limit the present disclosure. Variations may be made to the embodiments without departing from the spirit of the present disclosure as claimed. Elements associated with any of the above embodiments are envisioned to be associated with any other embodiments. The above-described embodiments illustrate the scope of the present disclosure but do not restrict the scope of the present disclosure.

What is claimed is:

1. An electrode lead of a pacemaker comprising at least one lead wire, wherein the at least one lead wire comprises at least one composite conductive core, the at least one composite conductive core comprises:
   at least one conductive core, the at least one conductive core being electrically conductive; and
   at least one carbon nanotube yarn spirally wound on an outer surface of the at least one conductive core, wherein the at least one carbon nanotube yarn comprises a plurality of carbon nanotubes joined end to end by van der Waals attractive forces;
   wherein the at least one composite conductive core comprises two opposite ends, a screw pitch of the spirally wound carbon nanotube yarn gradually increases from one end of the opposite ends to the other one of the opposite ends.

2. The electrode lead of claim 1, wherein the at least one carbon nanotube yarn comprises two opposite ends and a middle portion between the two opposite ends, the middle portion of the at least one carbon nanotube yarn is helical shaped, and at least one of the two opposite ends is substantially parallel with an extending direction of the conductive core.

3. The electrode lead of claim 1, wherein the screw pitch of the spirally wound carbon nanotube yarn is in a range from about 0 microns to about 5 microns.

4. The electrode lead of claim 1, wherein the at least one composite conductive core is helical shaped and forms a plurality of coils, a diameter of the plurality of coils is in a range from about 2 microns to about 6 microns.

5. The electrode lead of claim 1, wherein the at least one carbon nanotube yarn is combined with the at least one conductive core by van der Waals attractive forces.

6. The electrode lead of claim 1, wherein the at least one lead wire further comprises:
   an insulating layer disposed on an outer surface of the at least one composite conductive core, a distal end of the at least one composite conductive core is exposed out from the insulating layer;
   a shielding layer disposed on an outer surface of the insulating layer, and
   a coating layer disposed on an outer surface of the shielding layer.

7. The electrode lead of claim 1 further comprising an electrode tip electrically connected with a end of the at least one composite conductive core.

8. The electrode lead of claim 7, wherein the electrode tip comprises a porous film disposed on a surface of the electrode tip.

9. The electrode lead of claim 7, wherein the electrode tip is cylinder shaped or helical shaped.

10. A pacemaker comprising:
    a pulse generator, and
    an electrode lead electrically connected with the pulse generator, the electrode lead comprising at least one lead wire, wherein the at least one lead wire comprises at least one composite conductive core, the at least one composite conductive core comprises:
    at least one conductive core, the at least one conductive core being electrically conductive; and
       at least one carbon nanotube yarn spirally wound on an outer surface of the at least one conductive core, and wherein the at least one carbon nanotube yarn comprises a plurality of carbon nanotubes joined end to end by van der Waals attractive forces;
       wherein the at least one composite conductive core comprises two opposite ends, a screw pitch of the spirally wound carbon nanotube yarn gradually increases from one end of the opposite ends to the other one of the opposite ends.

11. The pacemaker of claim 10, wherein the at least at least one composite conductive core comprises a proximal end and a distal end opposite to the proximal end, the proximal end is electrically connected with the pulse generator, and the distal end is adapted to be located to electrically contact an organ.

12. The pacemaker of claim 11, wherein one end of the at least one carbon nanotube yarn is the distal end adapted to be located to directly contact the organ.

13. The pacemaker of claim 11, wherein one end of the at least one carbon nanotube yarn is the proximal end to electrically connect the pulse generator directly.

14. The pacemaker of claim 10, further comprising:

a connector to electrically connect the pulse generator and the electrode lead; and a fixture adapted to fix the electrode lead to be located to an organ.

15. The pacemaker of claim 14, wherein the fixture comprises a fixing ring and a plurality of fixing wings disposed on an outer surface of the fixing ring.

16. The pacemaker of claim 10, wherein the electrode lead further comprises an electrode tip electrically connected with one end of the at least one composite conductive core.

17. An electrode lead of a pacemaker comprising at least one lead wire, wherein the at least one lead wire comprises at least one composite conductive core, the at least one composite conductive core comprises:

at least one conductive core, the at least one conductive core being electrically conductive; and at least one carbon nanotube yarn spirally wound on an outer surface of the at least one conductive core, wherein a screw pitch of the spirally wound carbon nanotube yarn gradually increases along an extending direction, and the at least one carbon nanotube yarn comprises a plurality of carbon nanotubes joined end to end by van der Waals attractive forces.

\* \* \* \* \*